(12) United States Patent
O'Neill et al.

(10) Patent No.: US 9,562,621 B2
(45) Date of Patent: Feb. 7, 2017

(54) LINEAR DIGITAL PROPORTIONAL PIEZOELECTRIC VALVE

(71) Applicant: KONINKLIJKE PHILIPS N.V., Eindhoven (NL)

(72) Inventors: Francis Patrick O'Neill, Kissimmee, FL (US); Ronald Paul Consiglio, Clermont, FL (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/888,718

(22) PCT Filed: Apr. 23, 2014

(86) PCT No.: PCT/IB2014/060934
§ 371 (c)(1),
(2) Date: Nov. 3, 2015

(87) PCT Pub. No.: WO2014/181208
PCT Pub. Date: Nov. 13, 2014

(65) Prior Publication Data
US 2016/0053909 A1    Feb. 25, 2016

Related U.S. Application Data

(60) Provisional application No. 61/820,275, filed on May 7, 2013.

(51) Int. Cl.
*G01V 3/00*        (2006.01)
*F16K 31/00*       (2006.01)
(Continued)

(52) U.S. Cl.
CPC ........... *F16K 31/004* (2013.01); *A61B 5/0235* (2013.01); *A61M 16/202* (2014.02); *F16K 1/443* (2013.01);
(Continued)

(58) Field of Classification Search
CPC ...... F16K 31/004; F16K 1/443; F16K 11/044; F16K 31/005; A61M 16/202; A61B 5/0235; G01R 33/28
See application file for complete search history.

(56) References Cited

U.S. PATENT DOCUMENTS 6,230,738 B1 * 5/2001 Watanabe ............. F16K 31/004
                                                      137/486
6,684,904 B2   2/2004 Ito
(Continued)

FOREIGN PATENT DOCUMENTS

| EP | 1375846 A1 | 1/2004 |
| JP | 60057070 A | 4/1985 |
| JP | 2112669 A  | 4/1990 |

*Primary Examiner* — Daniel Miller

(57) ABSTRACT

An electrically controlled valve (10) includes a shaft (36), a piezoelectric motor (34) affixed to an end of the shaft (36), a controller (54), a follower (42), a valve member (40), and a valve seat (28). The piezoelectric motor (34) drives the shaft with a first direction and a second opposite direction. The controller (54) provides power to the piezoelectric motor (34) to move the shaft with a first speed and a second speed, the first speed being faster that the second speed. The follower (42) receives the shaft (36), and slides relative to the shaft in response to the shaft moving with the first speed, and grips and moves with the shaft in response to the moving with the second speed and includes a valve member (40). The valve member (40) moves with the follower (42). The valve member (40) is configured to be moved by the follower (42) against the valve seat (28) to restrict fluid flow and to be moved by the follower (42) away from the valve seat to increase the fluid flow.

20 Claims, 5 Drawing Sheets

(51) Int. Cl.
*F16K 11/044* (2006.01)
*A61M 16/20* (2006.01)
*A61B 5/0235* (2006.01)
*G01R 33/28* (2006.01)
*F16K 1/44* (2006.01)
*A61M 16/01* (2006.01)
*A61B 5/055* (2006.01)
*A61B 5/08* (2006.01)

(52) U.S. Cl.
CPC ........... *F16K 11/044* (2013.01); *F16K 31/005* (2013.01); *G01R 33/28* (2013.01); *A61B 5/055* (2013.01); *A61B 5/082* (2013.01); *A61B 2503/045* (2013.01); *A61B 2505/05* (2013.01); *A61M 16/01* (2013.01); *A61M 2205/057* (2013.01); *A61M 2230/30* (2013.01)

(56) References Cited

U.S. PATENT DOCUMENTS

| | | |
|---|---|---|
| 7,275,522 B2 | 10/2007 | Beilharz et al. |
| 8,191,857 B2 | 6/2012 | Hansen, III et al. |
| 2003/0226905 A1 | 12/2003 | Cotton, III et al. |
| 2007/0120442 A1 | 5/2007 | Piotr |
| 2011/0220821 A1 | 9/2011 | Hess |

* cited by examiner

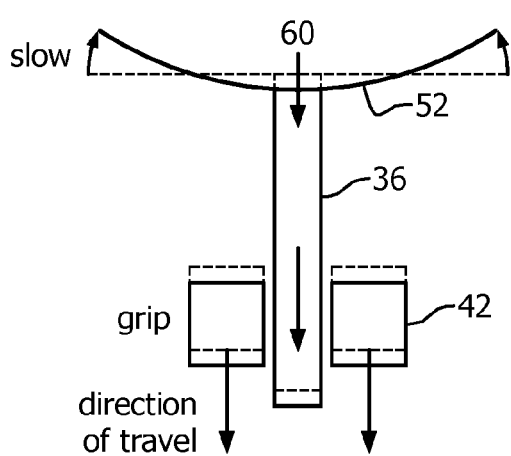
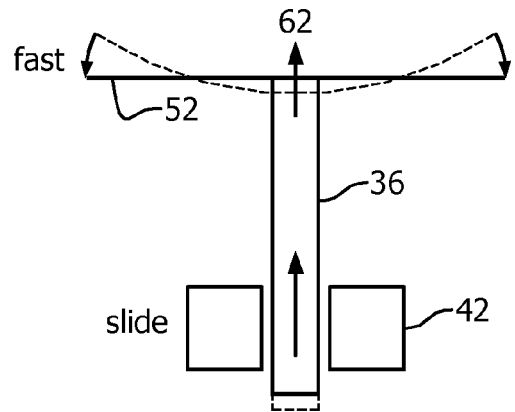
FIG. 3A    FIG. 3B
FIG. 3C
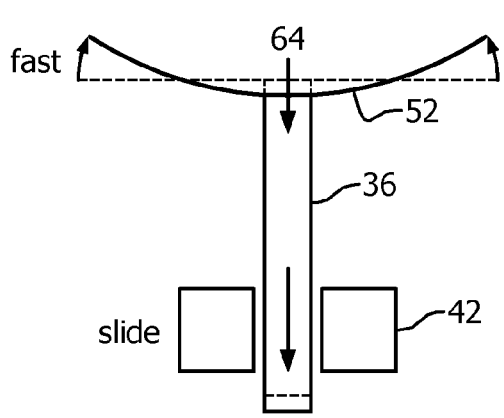
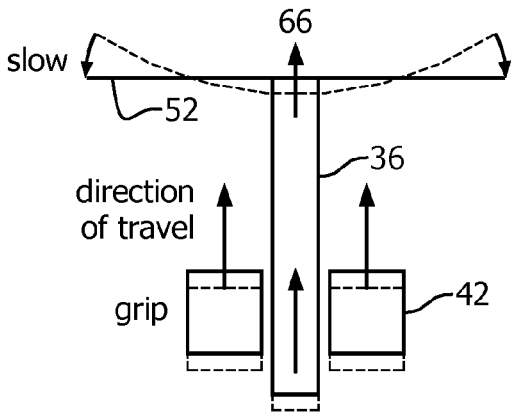
FIG. 4A    FIG. 4B
FIG. 4C

LINEAR DIGITAL PROPORTIONAL PIEZOELECTRIC VALVE

CROSS REFERENCE TO RELATED APPLICATIONS

This application is a national filing of PCT application Serial No. PCT/IB2014/060934, filed Apr. 23, 2014, published as WO 2014/181208 A1 on Nov. 13, 2014, which claims the benefit of U.S. provisional application Ser. No. 61/820,275 filed May 7, 2013, which is incorporated herein by reference.

BACKGROUND

The following relates generally to electrically controlled valves which can operate in a strong magnetic field. It finds particular application in conjunction with low-pressure fluid valves which operate near a magnetic resonance imaging scanner, and will be described with particular reference thereto. However, it will be understood that it also finds application in other usage scenarios and is not necessarily limited to the aforementioned application.

Electrically controlled valves with solenoids or ferrous parts are adversely affected near strong magnetic fields such as in a magnetic resonance (MR) room or in the bore of an MRI scanner. Valves which operate in a strong magnetic field include non-magnetic materials or are designed such that the magnetic materials are removed or shielded from the magnetic field. The presence of magnetic materials can affect operation of the valve device and can potentially act as projectiles. Valves are used for controlling fluids such as anesthesia gas supply during magnetic resonance guided surgery, air pressure control in non-invasive blood pressure (NIBP) monitoring, oxygen supply for patient life support, measuring patient gas expiration, and the like. One acute area of need includes neonatal applications where volumes of gas are small and close adjustment of fluid flow is important.

One approach is to use a valve switched pneumatically from a traditional valve location outside the magnetic field, e.g. located outside a shielded room with pneumatic connections. The disadvantage is the use of a compressed air supply, bulky pneumatic tubing, and noise. Another approach is the use of shielding to shield ferrous valve parts from external magnetic fields. However, shielding makes use of ferrous materials such as iron which make the shielding subject to distorting the magnetic field and becoming potentially projectiles.

Valves typically include a spring or biasing element which biases the valve by default either open or closed. Springs materials subject to the strong magnetic fields, and in some instances, can collapse under the magnetic forces. Alternatively, springs can be made from non-magnetic materials such as beryllium-copper or phosphor-bronze but the material is costly. Furthermore, the non-magnetic materials can be found to change their spring constant over time which makes them less reliable in medical care applications.

Another approach is the use of valve materials which are not subject to the magnetic field. For example, piezoelectric diaphragm valves are used, but are typically physically large and need very high drive voltages. The diaphragm includes a covering of piezoelectric material which operates to change shape and directly open or close a valve port when an electrical charge is applied. The high voltage drivers are expensive and difficult to implement in magnetic field because they often have components which are also subject the magnetic field. Another example includes piezoelectric bending actuators such as a flap which bends to directly open or close a valve. Both examples include a spring element or biasing element which is subject to wear and difficult to replace and/or repair. Both examples include a valve which operates in analog manner between the valve being either completely open or completely closed.

The following discloses a new and improved linear digital proportional piezoelectric valve which addresses the above referenced issues, and others.

BRIEF SUMMARY

In accordance with one aspect, an electrically controlled valve includes a shaft, a piezoelectric motor affixed to an end of the shaft, a controller, a follower, a valve member, and a valve seat. The piezoelectric motor drives the shaft with a first direction and a second opposite direction. The controller provides power to the piezoelectric motor to move the shaft with a first speed and a second speed, the first speed being faster that the second speed. The follower receives the shaft, and slides relative to the shaft in response to the shaft moving with the first speed, and grips and moves with the shaft in response to the moving with the second speed and includes a valve member. The valve member moves with the follower. The valve member is configured to be moved by the follower against the valve seat to restrict fluid flow and to be moved by the follower away from the valve seat to increase the fluid flow.

In accordance with another aspect, a method of fluid control includes applying electrical pulses to a piezoelectric motor which moves a shaft affixed to the piezoelectric motor to move the shaft with a first speed and a second speed, the second speed being faster than the first speed. The shaft is moved with the second speed such that a follower which receives the shaft slides relative to the shaft. The shaft is moved with the first speed such that the follower grips the shaft and moves with the shaft. Pulses are repeatedly applied to alternately move the shaft away toward a valve seat at the first speed and away from the valve seat at the second speed to move a valve member which moves with the follower against a valve seat to restrict fluid flow. Pulses are repeatedly applied to alternately move the shaft toward a valve seat at the second speed and away from the valve seat at the first speed to move the valve member which moves with the follower away from the valve seat to increase fluid flow.

In accordance with another aspect, an electrically controlled valve which operates in a strong magnetic field includes a rod, a follower located circumferentially adjacent to the rod, a valve element attached to the follower, a valve member attached to the valve element, and a magnetic field inert housing. The follower allows the rod to overcome friction forces with the follower with a first force applied to the rod and slide along the rod, and to grip and move with the rod in response to a second applied opposing force. The valve element defines a central well shaped cavity to receive the rod. The magnetic field inert housing defines a cavity that holds the follower and the valve element, receives the rod, and defines a first port connected to the cavity, a second port connected to the cavity, and a seat. The first port receives fluid inflow. The second port outflows the received fluid. The seat receives the valve member and restricts the fluid flow between the first port and the second port proportional to the distance from the valve member to the seat.

One advantage is low power consumption.

Another advantage includes a low hysteresis.

Another advantage resides in a low cost of manufacture.

Another advantage resides in low back pressure and low differential pressure.

Another advantage resides in ease of control without voltage control.

Another advantage resides in digital operation, particularly digital control of a degree to which the valve is open.

Another advantage resides in the simple construction without a spring or biasing element.

Still further advantages will be appreciated to those of ordinary skill in the art upon reading and understanding the following detailed description.

BRIEF DESCRIPTION OF THE DRAWINGS

The invention may take form in various components and arrangements of components, and in various steps and arrangement of steps. The drawings are only for purposes of illustrating the preferred embodiments and are not to be construed as limiting the invention.

FIGS. 3A-3C schematically illustrates in one embodiment of linear digital proportional piezoelectric forces, a direction of linear movement, and an associated electrical driver pulse intensity shape.

FIGS. 4A-4C schematically illustrates the linear digital proportional piezoelectric forces, an opposite direction of linear movement, and an associated electrical pulse intensity shape.

DETAILED DESCRIPTION

Figure 1:
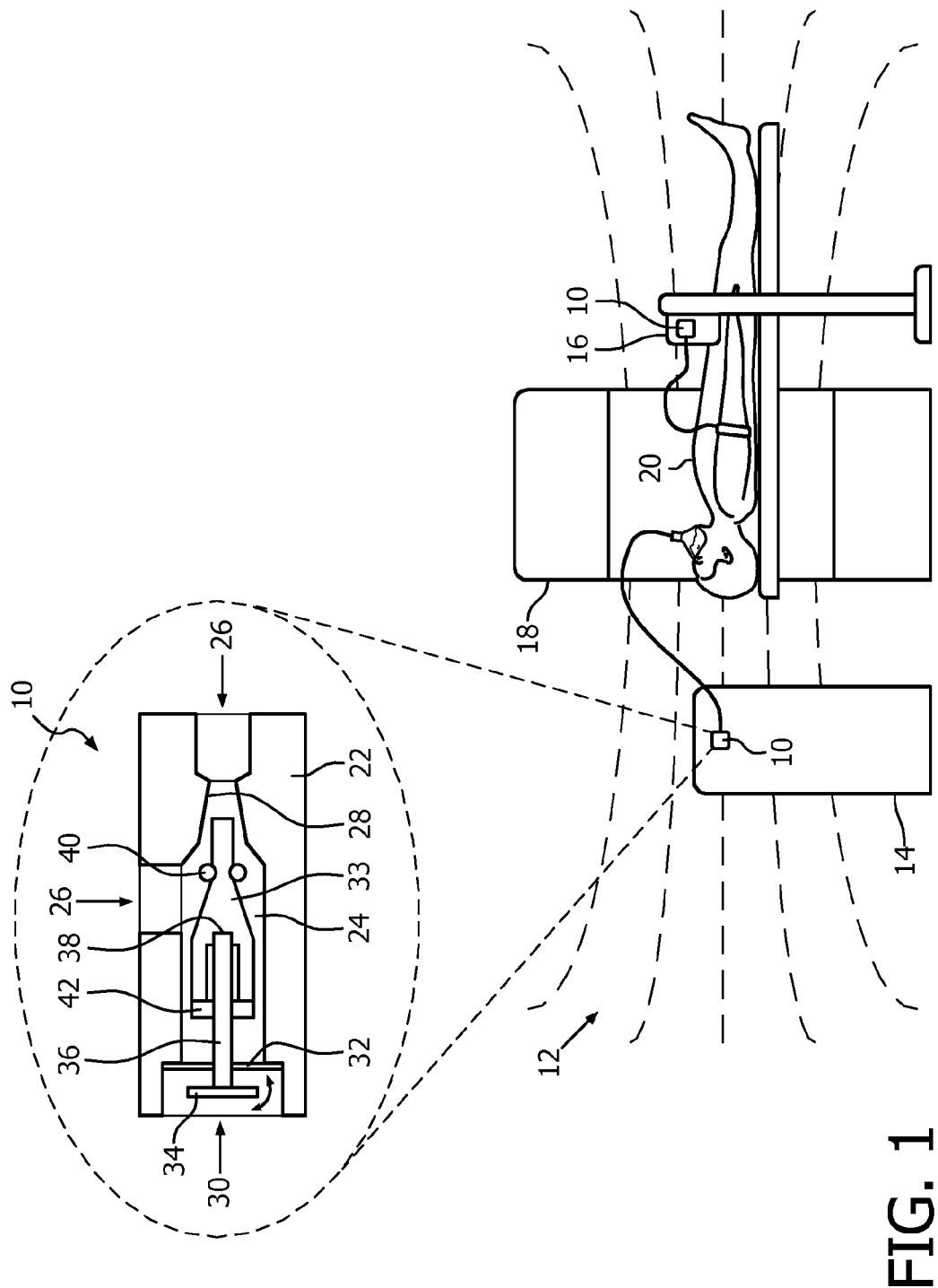
FIG. 1 schematically illustrates an embodiment of a linear digital proportional piezoelectric valve in a strong magnetic field with an exploded cross section view of the linear digital proportional piezoelectric valve.

With reference to FIG. 1, an embodiment of a linear digital proportional piezoelectric valve 10 in a strong magnetic field 12 with an exploded cross section view of the linear digital proportional piezoelectric valve is schematically illustrated. Two medical devices are shown, by way of example, with the linear digital proportional piezoelectric valve 10, an anesthesia device 14 and a non-invasive blood pressure (NIBP) measuring device 16. A magnetic resonance scanner 18 is shown in partial cross section which generates strong magnetic fields such as a static main magnetic field $B_0$, gradient magnetic fields, RF pulses $B_1$, and the like. Typical applications of the linear digital proportional piezoelectric valve include regulating the delivery of fluids such as anesthetic gases to a subject 20, monitoring gases expired by the subject, monitoring NIBP, and the like. The illustrated valve is designed to operate up to about 0.68 atm (10 psi; 0.69 bar) which makes it suitable for these types of applications. The application can include regulating gases for neonatal applications such as NIBP which differ from adult NIBP by orders of magnitude.

The valve 10 includes a valve housing 22 of MR inert material such as plastic. The housing 22 defines an internal cavity 24 with two ports 26, one for inflow of fluids such as anesthetic gases, respiratory gases, air, etc. and one for outflow. The ports can operate in either direction. The base defines a valve seat 28 and an access opening 30 covered by a bonnet 32. The cavity receives a valve element 33 through the access opening, e.g. the valve member is positioned within the cavity 24. The valve element defines a central well shaped cavity 38 to receive a drive rod 36.

A piezoelectric motor 34 is affixed to an end of the drive rod or shaft 36 opposite the follower and the rod passes through an opening in the seal 32 into an interior of the valve element 33. For example, the motor and rod form a nail shape with piezoelectric material affixed to a surface of the nail head. The piezoelectric motor drives the rod based on received pulses of electric current with a first current intensity which applies a first force to the rod and a second current intensity which applies an opposing second force to the rod. For example, a first current intensity flexes piezoelectric material quickly which applies a first force to the rod. A second current intensity flattens the piezoelectric material slowly which applies an opposing second force to the rod. In another example, a first current intensity flexes the piezoelectric material slowly which applies one force, and a second current intensity flattens the piezoelectric material quickly which applies another opposing force. The rod 36 can include materials such as copper, aluminum, and the like.

A follower 42 moves linearly along the length of the rod driven by the piezoelectric motor to open or close the valve 10. In the closed position, the valve seat 28 receives a valve member 40, such as an O-ring and restricts the fluid flow between the ports proportional to a displacement between the valve member 40 to the valve seat 28. For example, the valve is fully closed with the valve member compressed against the seat. The valve can be partially opened by applying a fixed number of electrical pulses to the piezoelectric motor to partially open the valve. The valve can be fully open by the movement of the follower such that the end of the rod opposite the piezoelectric motor engages the bottom of the well 38 defined in the valve element. The position of follower with the rod engaging the well bottom fully opens the valve and permits fluid flow between the ports. The drawing depicts the valve in a fully open configuration.

The follower 42 which slides along the rod 36 in response to a force exerted by the piezoelectric motor on the rod which overcomes friction, such as with fast flexing or fast flattening of the piezoelectric material. The follower 42 grips and moves with the rod 36 in response to a force exerted by the piezoelectric motor which moves the rod with insufficient speed to overcome friction such as with slow flexing or slow flattening of the piezoelectric material. The follower 42 attaches to the valve element 33 and is located circumferentially and frictionally engaging the rod 36. The follower 42 can include material such as tin, copper, brass, rubber, plastic and the like.

Figure 2:
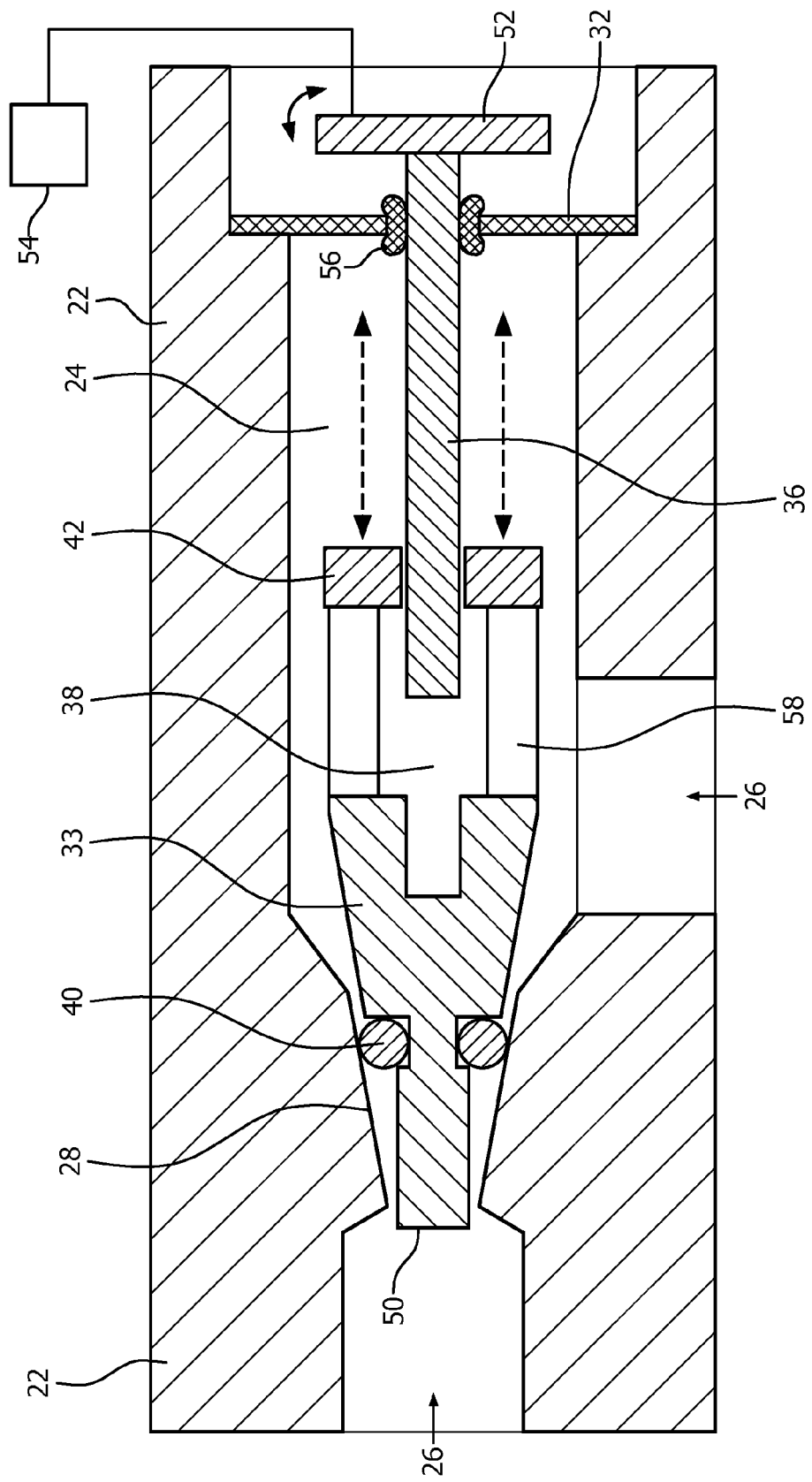
FIG. 2 schematically illustrates one embodiment of the linear digital proportional piezoelectric valve in cross section.

With reference to FIG. 2, one embodiment of the linear digital proportional piezoelectric valve 10 is schematically illustrated in cross section. The valve 10 is shown in a fully closed configuration where the valve member 40 is received by the seat 28 and restricts the flow between the ports 26. The seat 28 and the valve member 40 can be tapered for a closer fit. The valve element 33 can include a nose guide 50 which guides the valve member 40 to the seat and keeps the follower and valve element correctly positioned within the cavity 24.

The piezoelectric motor includes a piezoelectric material wafer 52 attached to the end of the rod 36. The piezoelectric motor includes a microcontroller 54 connected to the piezoelectric material 52 which provides electrical pulses to flex and flatten the piezoelectric material 52 according to the distance and direction of travel for the follower 42. A retainer ring 56 of rubber or other suitable flexible and/or low friction material can be used as a retainer.

The follower 42 can be driven by the piezoelectric motor in discrete distances and different directions. For example, each pulse moves the follower a discrete distance along the rod or shaft 36 in a ratchet-like action. The follower is moved by the piezoelectric motor discrete steps. The piezoelectric motor can be overdriven to ensure a tight seal between the valve member and the valve seat in the close position.

Arms 58 attach the follower 42 to the valve element 33. The arms can be spaced to allow fluid flow into the cavity 24 as the shaft is received into the well 38.

With reference to FIGS. 3A-3C, one embodiment of linear digital proportional piezoelectric motor, a direction of linear movement, and an associated electrical pulse intensity shape are schematically illustrated. Example current pulses are shown in FIG. 3C with the intensity of the current pulses slowly increasing and quickly decreasing. The slow intensity increase flexes the piezoelectric material 52 slowly as illustrated in FIG. 3A which exerts a force on the shaft 36 to move the shaft in a discrete distance. The follower 42 frictionally grips the shaft 36 and moves with the shaft in a direction of travel. With the quick decrease in intensity of the electrical pulse as shown in FIG. 3C, the piezoelectric material 52 flattens quickly as shown in FIG. 3B. The fast flattening of the piezoelectric material 52 exerts an opposing force 62 on the shaft with a speed which is sufficient to overcome friction forces between the follower 42 and the shaft. The follower 42 and the valve element 33 remain relatively motionless while the shaft moves opposite to the direction of FIG. 3A and slides past the follower.

The example repeated discrete number of pulses of FIG. 3C move the follower a discrete number of steps, i.e. a discrete distance in the direction of travel as shown in FIG. 3A. The travel distance is linear along the shaft and proportional to the number of electrical pulses. No voltage control is needed. In the illustrated embodiment, the pulses operate to move the follower to a closed or partially closed configuration. The degree of closure is based on the distance between the valve member and the seat.

With reference to FIGS. 4A-4C, the direction of travel is reversed. FIG. 4C illustrates the intensity curves of the electrical pulses which drive the piezoelectric motor. The illustrated pulses include a sharp increase in intensity followed by a slow decrease in intensity. The sharp increase flexes the piezoelectric material 52 quickly as shown in FIG. 4A which drives the shaft with a speed 64 sufficient to overcome the friction forces between the shaft 36 and the follower 42. The shaft slides a discrete distance past the follower as determined by the flex distance of the piezoelectric wafer. The slow decrease flattens the piezoelectric material 52 slowly which exerts a force 66 opposite of that in FIG. 4A, but with a speed insufficient to overcome the friction forces between the shaft and the follower. The shaft moves in the direction of travel gripped by the follower 42 which moves the valve element a discrete amount in the direction of travel. The direction of travel is toward an open or partially open configuration.

In one embodiment, the microcontroller limits the opening a discrete amount such as appropriate for neonatal applications. A partial opening allows fluids flow between the ports, but at a limited or proportional amount. In another embodiment, the valve can be primed a discrete amount to move from a fully closed configuration to a partial opening.

Figure 5B:
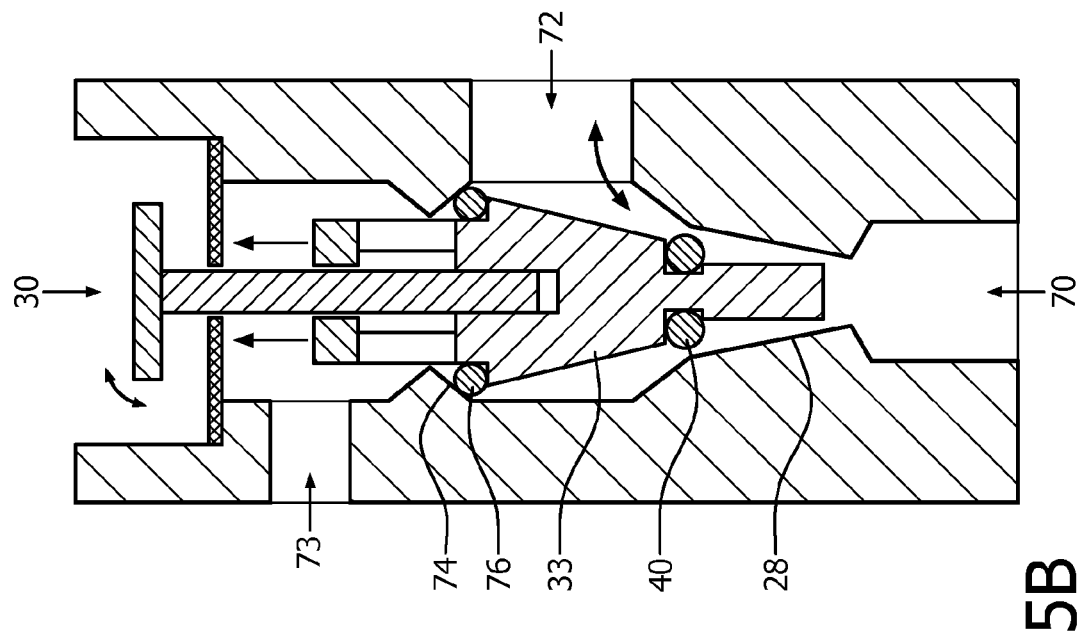
FIGS. 5A-5B schematically illustrates an embodiment of a 3-way linear digital proportional piezoelectric valve in cross-section in two configurations.
Figure 5A:
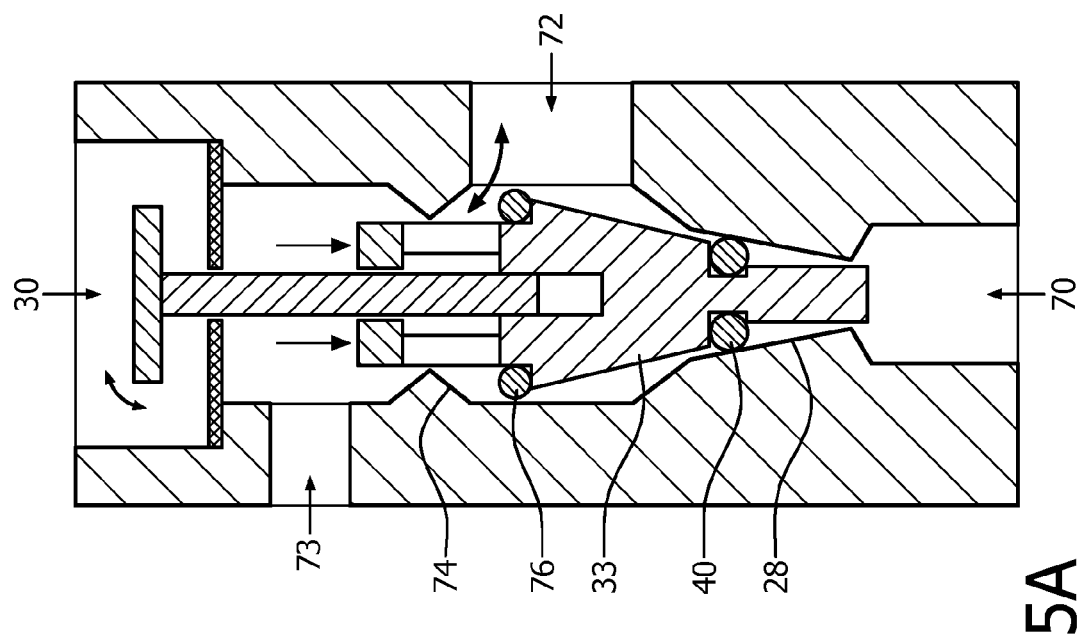

With reference to FIGS. 5A and 5B, an embodiment of a 3-way linear digital proportional piezoelectric valve in cross-section is shown in two configurations. A first port 70 with fluid flow restricted from a second port 72 by the valve member 40 and the seat 28. A third port 73 connects with the second port 72 with fluid flow restricted by a second seat 74 and a second valve member 76.

In FIG. 5A, the valve is shown configured with a fluid opening between the second or central port 72 and the third port 73 open to fluid flow. The valve member 40 is configured adjacent to the seat 28 which closes the first or end port 70.

In FIG. 5B, the valve is shown configure with a fluid opening between the second port 72 and the first port 70. The valve member 40 is separated from the seat 28, while the second valve member 76 engages the second seat 74. The fluid flow to the third port 73 is closed by the second valve member 76 engaging the second seat 74.

In between the positions shown in FIGS. 5A and 5B fluid flow entering port 72 is divided between ports 70 and 73 in proportion to the location of the valve members. In another embodiment, the follower is configured with a tapered second valve element and the gripping mechanism is located between the valve member 40 and the second valve member 76. Other embodiments of the 3-way valve are contemplated without the well of the follower because the second valve member and second seat act to limit the position of the follower within the cavity.

Figure 6:
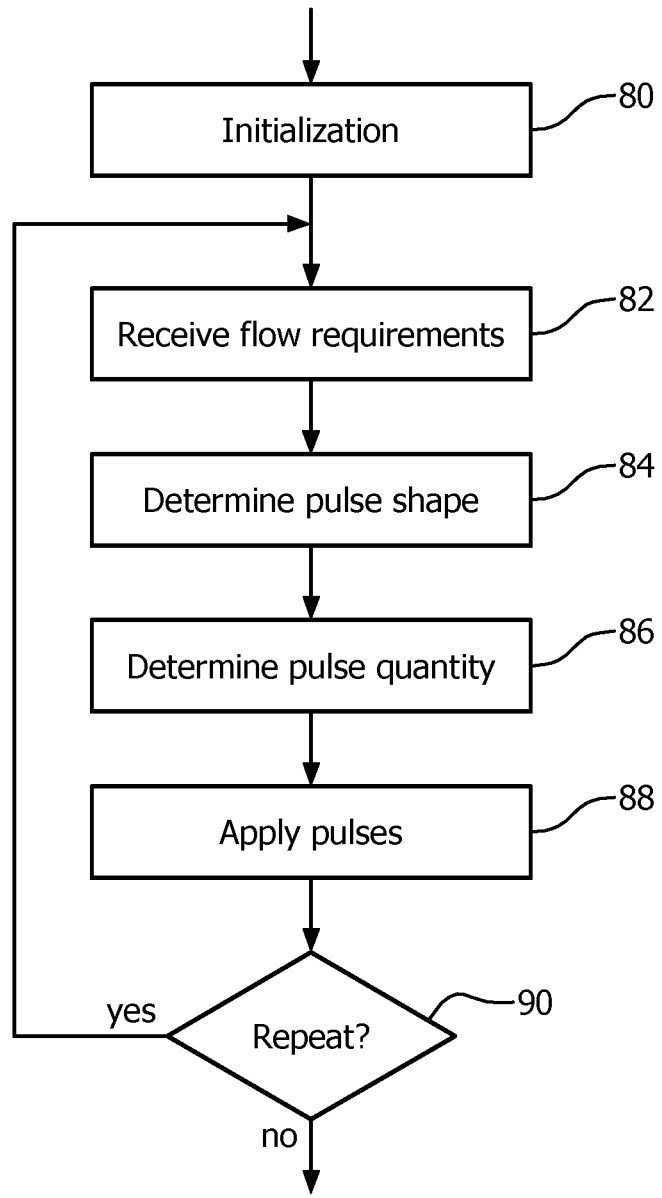
FIG. 6 flowcharts one method of using an embodiment of the linear digital proportional piezoelectric valve.

With reference to FIG. 6 one method of using an embodiment of the linear digital proportional piezoelectric valve is flowcharted. In a step 80, valve initialization is performed. The step can include priming the valve with a predetermined number of electrical pulses. The step can include determining limits of the valve opening and/or closing such as with neonatal applications. The valve is non-magnetic and can be positioned in a magnetic field such as a MRI without adverse effect.

Flow requirements are received in a step 82. The flow requirements include a direction and distance of travel of the valve element 33. The flow requirements are received by the microcontroller which controls the piezoelectric motor. For example, the current position of the valve configured as a two way valve is closed and the flow requirements include opening the valve an amount such as x where x is expressed as a distance and direction of change in position of the follower. A flow requirement expressed as a volumetric amount can be converted to a distance and direction based on the valve size and physical characteristics. The valve element restricts the fluid flow between a first port and a second port the discrete amount proportional to the opening size which is proportional to the distance from the valve member to the valve seat.

A pulse shape is determined in a step 84. The pulse shape drives the piezoelectric material to flex at a first rate with a first predetermined current intensity and flatten at a second rate with a second predetermined current intensity. The relationship between the current intensity and the direction of travel of the follower are described previously in reference to FIGS. 3A-3C and FIGS. 4A-4C.

A quantity of pulses is determined in a step 86 which further restricts or opens the fluid flow through the valve a discrete amount. The quantity of pulses operate the piezoelectric motor to move the follower in a ratchet-like motion a discrete distance based on the received flow requirements.

In a step 88, the determined pulse shape and pulse quantity are applied to the piezoelectric material of the valve which moves the follower the discrete distance. The piezoelectric material is affixed to and centered on an end of a shaft. The follower receives the shaft and moves with the valve member. The follower allows the shaft to overcome friction forces and slide in response to a fast flexing or a fast flattening of the piezoelectric material. The shaft can include copper, aluminum, plastic, and the like. The gripping mechanism grips and moves with the shaft in response to a slow flexing or a slow flattening of the piezoelectric material. The gripping mechanism includes tin, copper, brass, rubber, plastic and the like. The follower restricts the fluid flow between the ports the discrete amount proportional to a distance from the valve member to the seat. The fluid flow is based on the linear movement of the follower operated digitally by the piezoelectric motor based on the pulse shape which determines direction and the pulse quantity which determines distance. The distance and direction discretely open and/or close the valve according to the received fluid requirements.

The movement of the follower can be limited by engaging an end of the shaft opposite in the bottom of the well 38 or engaging the second seat 72 with the second valve member 76, or limiting the movement of the follower by engaging the valve seat 28 with the valve member 40. Additional electrical pulses can be applied to ensure a pressure seal of the seat and valve member. The time to actuate or change position is fast such as 6-8 ms.

In a decision step 90, a change in the opening and/or closing of the valve is decided. With a change in the valve opening/closing which includes a change in position of the follower, the previous steps can be repeated. For example, with a current position of the valve as closed and flow requirements are received which call for a fully open valve, the change in position of the follower which meets the flow requirements can be determined, the pulse shape and quantity of pulses determined, and the pulses applied to fully open the valve. Alternatively, a flow monitor is disposed downstream of the valve. The controller 54 adjusts the valve opening to being the actual flow or pressure measured by the monitor into conformity with a preselected flow.

It is to be appreciated that in connection with the particular illustrative embodiments presented herein certain structural and/or function features are described as being incorporated in defined elements and/or components. However, it is contemplated that these features may, to the same or similar benefit, also likewise be incorporated in other elements and/or components where appropriate. It is also to be appreciated that different aspects of the exemplary embodiments may be selectively employed as appropriate to achieve other alternate embodiments suited for desired applications, the other alternate embodiments thereby realizing the respective advantages of the aspects incorporated therein.

It is also to be appreciated that particular elements or components described herein may have their functionality suitably implemented via hardware, software, firmware or a combination thereof. Additionally, it is to be appreciated that certain elements described herein as incorporated together may under suitable circumstances be stand-alone elements or otherwise divided. Similarly, a plurality of particular functions described as being carried out by one particular element may be carried out by a plurality of distinct elements acting independently to carry out individual functions, or certain individual functions may be split-up and carried out by a plurality of distinct elements acting in concert. Alternately, some elements or components otherwise described and/or shown herein as distinct from one another may be physically or functionally combined where appropriate.

In short, the present specification has been set forth with reference to preferred embodiments. Obviously, modifications and alterations will occur to others upon reading and understanding the present specification. It is intended that the invention be construed as including all such modifications and alterations insofar as they come within the scope of the appended claims or the equivalents thereof. That is to say, it will be appreciated that various of the above-disclosed and other features and functions, or alternatives thereof, may be desirably combined into many other different systems or applications, and also that various presently unforeseen or unanticipated alternatives, modifications, variations or improvements therein may be subsequently made by those skilled in the art which are similarly intended to be encompassed by the following claims.

What is claimed is:

1. An electrically controlled valve, comprising:
   a shaft;
   a piezoelectric motor affixed to an end of the shaft and drives the shaft in a first linear direction and a second opposite linear direction;
   a controller which provides power to the piezoelectric motor to move the shaft with a first speed and a second speed, the first speed being faster that the second speed;
   a follower which receives the shaft, and slides relative to the shaft in response to the shaft moving with the first speed, and grips and moves with the shaft in response to the moving with the second speed;
   a valve member which moves with the follower; and
   a valve seat, the valve member is configured to be moved by the follower against the valve seat to restrict fluid flow and to be moved by the follower away from the valve seat to increase the fluid flow.

2. The electrically controlled valve according to claim 1, wherein the follower circumferentially surrounds the shaft, and the shaft and the follower are configured to allow the shaft to overcome friction forces and slide in response to relative motion at the first speed, and grip and move together in response to relative motion at the second speed.

3. The electrically controlled valve according to claim 1, further including:
   a second valve member connected with the follower.

4. The electrically controller valve according to claim 1, further including:
   a housing which defines a cavity, the valve seat and a first valve port and a second valve port connected to the cavity and separated by the valve seat.

5. The electrically controller valve according to claim 1, further including:
   a second valve member which moves with the follower; and
   wherein the housing further defines a third port connected to the cavity and a second valve seat which separates the third port from the first and second ports, the second valve member moves against the second valve seat to restrict fluid flow of the third port and the second valve member moves away from the second valve seat to increase fluid flow of the third port.

6. The electrically controlled valve according to claim 1, wherein the housing, the piezoelectric motor, the follower, the valve member, and the valve seat are magnetically inert.

7. The electrically controlled valve according to claim 1, further including:

a valve element connected to the follower and the valve member, the valve element defining a central well which receives the shaft such that a bottom of the well engages an end of the shaft in a fully open configuration of the electrically controlled valve.

8. The electrically controlled valve according to claim 7, wherein the valve element further includes:
a nose guide extending from the valve member which guides the valve member into the seat.

9. A magnetic resonance (MR) system, comprising:
a MR imager;
a gas supply system; and
the electrically controlled valve according to claim 1.

10. A method of fluid control, comprising:
applying electrical pulses to a piezoelectric motor which moves a shaft affixed to the piezoelectric motor to move the shaft with a first speed and a second speed, the second speed being faster than the first speed;
moving the shaft with the first speed such that a follower which receives the shaft slides relative to the shaft;
moving the shaft with the second speed such that the follower grips the shaft and moves with the shaft;
repeatedly applying pulses to alternately move the shaft toward a valve seat at the second speed and away from the valve seat at the first speed to move a valve member which moves with the follower against the valve seat to restrict fluid flow; and
repeatedly applying pulses to alternately move the shaft toward the valve seat at the first speed and away from the valve seat at the second speed to move the valve member which moves with the follower away from the valve seat to increase the fluid flow.

11. The method according to claim 10, further including:
determining an electrical pulse shape for the piezoelectric motor to drive the shaft with the first speed in one direction and the second speed in the opposite direction;
determining a quantity of electrical pulses which change the fluid flow by a discrete amount.

12. The method according to claim 10, wherein the piezoelectric motor includes piezoelectric material and in response to applying the electrical pulses:
flexing the piezoelectric material at a first rate to drive the shaft with the first speed, and flattening the piezoelectric material at a second rate to drive the shaft with the second speed to move the follower toward the piezoelectric motor.

13. The method according to claim 10, wherein the piezoelectric motor includes piezoelectric material and in response to applying the electrical pulses:
flexing the piezoelectric material at a first rate to drive the shaft with the second speed, and flattening the piezoelectric material at a second rate to drive the shaft with the first speed to move the follower away from the piezoelectric motor.

14. The method according to claim 10, wherein the follower is connected with a second valve member; and in response to applying the electrical pulses:
restricting the fluid flow between a first port and a third port proportional to the distance from the second valve member to a second seat.

15. The method according to claim 10, wherein applying further includes:
applying additional electrical pulses to ensure a pressure seal of the valve seat and the valve member.

16. The method according to claim 10, wherein applying further includes:
performing a valve initialization including selecting a discrete valve opening by the number of electrical pulses applied based on a predetermined opening limit.

17. The method according to claim 10, further including:
performing a valve initialization including priming with a predetermined number of applied electrical pulses.

18. An electrically controlled valve comprising:
a shaft;
a piezoelectric motor affixed to an end of the shaft and drives the shaft with a first direction and a second opposite direction, wherein the piezoelectric motor further includes piezoelectric material which flexes at a first rate to drive the shaft with the first speed and flattens at a second rate to drive the shaft with the second speed;
a controller which provides power to the piezoelectric motor to move the shaft with a first speed and a second speed, the first speed being faster that the second speed;
a follower which receives the shaft, and slides relative to the shaft in response to the shaft moving with the first speed, and grips and moves with the shaft in response to the moving with the second speed;
a valve member which moves with the follower; and
a valve seat, the valve member is configured to be moved by the follower against the valve seat to restrict fluid flow and to be moved by the follower away from the valve seat to increase the fluid flow.

19. An electrically controlled valve according to claim 18, wherein the controller is connected to the piezoelectric material and applies electrical pulses to selectively flex and flatten the piezoelectric material at the first rate and the second rate to move the shaft with the first and second speeds, respectively.

20. A magnetic resonance (MR) system, comprising:
a MR imager;
a gas supply system; and
the electrically controlled valve according to claim 18.

* * * * *